(12) United States Patent
Faulkner et al.

(10) Patent No.: US 11,529,468 B2
(45) Date of Patent: Dec. 20, 2022

(54) SYRINGE FOR ADMINISTERING FOAM (71) Applicant: PROVENSIS LIMITED, London (GB)

(72) Inventors: David Faulkner, London (GB); Daniel Isler, London (GB)

(73) Assignee: PROVENSIS LIMITED, London (GB)

( * ) Notice: Subject to any disclaimer, the term of this patent is extended or adjusted under 35 U.S.C. 154(b) by 619 days.

(21) Appl. No.: 16/320,599

(22) PCT Filed: Jul. 20, 2017

(86) PCT No.: PCT/IB2017/054404
§ 371 (c)(1),
(2) Date: Jan. 25, 2019

(87) PCT Pub. No.: WO2018/020367
PCT Pub. Date: Feb. 1, 2018

(65) Prior Publication Data
US 2019/0167907 A1   Jun. 6, 2019

(30) Foreign Application Priority Data

Jul. 26, 2016  (GB) ..................... 1612948

(51) Int. Cl.
*A61M 5/315* (2006.01)
*A61M 5/178* (2006.01)
(Continued)

(52) U.S. Cl.
CPC ....... *A61M 5/315* (2013.01); *A61B 17/00491* (2013.01); *A61B 17/12181* (2013.01);
(Continued)

(58) Field of Classification Search
CPC .... A61B 17/12181; A61M 2005/3123; A61M 2005/3114; A61M 5/315; A61M 5/178;
(Continued)

(56) References Cited

U.S. PATENT DOCUMENTS 3,540,448 A * 11/1970 Sunnen ................ A61M 31/00
  604/237
3,774,811 A * 11/1973 Staerman ............ B29C 44/3442
  222/190
(Continued)

FOREIGN PATENT DOCUMENTS

CN   1878706 B   12/2006
FR   2775436 A1   9/1999
(Continued)

OTHER PUBLICATIONS

International Search Report for International Application No. PCT/IB2017/054404, dated Jan. 4, 2018 (two pages).
(Continued)

*Primary Examiner* — Bhisma Mehta
*Assistant Examiner* — John J Crawford
(74) *Attorney, Agent, or Firm* — Seager, Tufte & Wickhem LLP (57) ABSTRACT Syringes which are suitable for dispensing and injecting medical foams for sclerotherapy are described and claimed. The syringes of the invention comprise a syringe barrel having a nozzle and a bore to receive a syringe plunger; a syringe plunger defined by a front end and a rear end connected by a tubular walls and having an internal hollow duct between the front end and the rear end, and through which foam can flow; and an injectate chamber formed by insertion of the front end of the plunger into the barrel. The syringes comprise a flow-disruptor arranged to modify the flow of foam as it enters the injectate chamber. In certain embodiments the syringes comprise waste chambers which capture and retain poor quality foam. The syringes are particularly useful for dispensing foams made with little or no nitrogen content and are configured to reduce the risk of air contamination during dispensing the foam. Kits comprising the syringes together with a suitable source of foam (Continued)

and methods of dispensing foam form further aspects of the invention.

16 Claims, 5 Drawing Sheets

(51) Int. Cl.
*A61M 5/31* (2006.01)
*A61M 5/34* (2006.01)
*A61B 17/12* (2006.01)
*A61B 17/00* (2006.01)

(52) U.S. Cl.
CPC .......... *A61M 5/178* (2013.01); *A61M 5/1782* (2013.01); *A61M 5/3129* (2013.01); *A61M 5/3148* (2013.01); *A61M 5/34* (2013.01); *A61M 2005/3114* (2013.01); *A61M 2005/3123* (2013.01)

(58) Field of Classification Search
CPC .................. A61M 5/19; A61M 39/225; A61M 2005/31521; A61M 2005/31523
See application file for complete search history.

(56) References Cited

U.S. PATENT DOCUMENTS

| | | | |
|---|---|---|---|
| 5,735,825 A * | 4/1998 | Stevens | A61M 5/31513 604/218 |
| 7,814,943 B2 * | 10/2010 | Harman | B65D 83/756 141/301 |
| 2007/0112308 A1 * | 5/2007 | Kay | B01F 13/0023 604/187 |
| 2007/0244429 A1 | 10/2007 | Nguyen et al. | |
| 2013/0045523 A1 | 2/2013 | Leach et al. | |
| 2016/0114106 A1 | 4/2016 | Kay et al. | |

FOREIGN PATENT DOCUMENTS

| | | |
|---|---|---|
| JP | 2007504872 A | 3/2007 |
| WO | WO 2004/039439 A2 | 5/2004 |
| WO | 2005023678 A1 | 3/2005 |

OTHER PUBLICATIONS

Written Opinion of the International Searching Authority for International Application No. PCT/IB2017/054404 (seven pages).

* cited by examiner

SYRINGE FOR ADMINISTERING FOAM

This application is a national stage filing under 35 U.S.C. § 371 of International Application No. PCT/IB2017/054404, filed on Jul. 20, 2017, which claims priority of British Patent Application No. 1612948.8, filed on Jul. 26, 2016. The contents of these applications are each incorporated herein by reference.

The present invention relates to syringes which are suitable for dispensing medical foams and, in particular, for the delivery of injectable microfoam from a source of foam to a patient in a way which minimizes the risk of air contamination. The invention also relates to methods for filling, or charging, the syringe with injectable foam for administration to a patient e.g. in the treatment of varicose veins or other venous disorders.

The treatment of varicose veins with sclerosing foams is a common procedure and whilst there are many advantages associated with foam sclerotherapy (e.g. a non-surgical procedure, no requirement for anaesthesia), there are safety concerns associated with the use of air to make such foams Nitrogen, the main constituent of air, is insoluble in blood and can cause gas embolism in patients. As a result, injectable foams have been produced which contain little or no nitrogen. WO 2005/048977 describes injectable microfoam made with physiologically acceptable gas in which the amount of nitrogen is controlled to between 0.0001 and 0.8% by volume. Foams produced with this range of nitrogen have been shown to be safe and efficacious in the treatment of varicose veins. The foam is typically produced from pressurised canister device of the type described in WO 00/72821 and WO02/41872. Although the canister devices control nitrogen content to the levels shown to be safe, the administering physician must take steps to avoid the introduction or co-injection of air as the low-nitrogen foam is transferred from the canister to a syringe for injection. Typically, the physician manually purges the syringe of air and an initial volume of foam to avoid air contamination.

WO 2005/053776 describes syringes which are suitable for dispensing injectable foam directly from pressurised canisters such as those described above. The syringe devices comprise means to ensure that air and/or any initial quantities of foam of inadequate quality are diverted into a waste chamber. Once a suitable volume of foam has been diverted to waste, the syringe is filled with foam of the necessary quality for administration to a patient.

The present inventors have made and tested the devices described in WO 2005/053776 and have established that a number of technical problems need to be overcome when developing the syringes for commercial and medical use. These include:

1. When foam is produced from a pressurised source (canister), there is an observed "mushrooming" of the foam from the point at which it leaves the constrained geometry of the canister outlet and enters the expanded volume of the injectate chamber/syringe barrel. Without wishing to be bound by theory, it appears that the cohesive nature foam causes foam to enter the injectate chamber in what appears to be a self-supporting column of foam and, at some point, the column is no longer self-supporting and the column collapses in a radially outward direction (hence the observed mushroom shape). The flowing foam tends to traps air as the chamber is filled. Turbulent mixing of the foam is also observed as the chamber fills, such that foam can break down, leaving sclerosant liquid and gas trapped within the injectate chamber. Not only is this sub-optimal with respect to trapped air but it may also have consequences for dose accuracy.
2. The methods described in WO 2005/053776 utilise the fact that foam entering the syringe is under pressure and the pressure of foam will force the syringe plunger outwards from the barrel, after the waste chamber is filled with foam. However, it has been established that, with certain syringe types, the pressure of the foam entering the syringe is sufficiently high to force the plunger to be ejected completely from the barrel, such that foam either cannot be dispensed accurately or is exposed to air. Typically, when this occurs the dose of foam is wasted and the foam and syringe have to be discarded.
3. The above issue is exacerbated with smaller syringes which are required for certain applications e.g. for treating of small diameter, superficial veins (commonly referred to as spider and reticular veins)
4. Although issues relating to pressure may be overcome to some degree by filling the syringe with the plunger pulled back to the desired volume to be collected (a "pre-cracked" syringe), the injectate chamber is then completely filled with air which needs to be purged. The problem described in 1) above is then exacerbated as a higher volume of air needs to be purged and air is routinely trapped in the injectate chamber.

Clearly, it is desirable to overcome these problems to ensure that low nitrogen injectable foams are not contaminated with air during the step of dispensing the foam. It is also desirable that any device for dispensing foam is simple to use, such that the dispensing physician can administer foam with confidence that the foam he is administering is unchanged from the foam he has produced.

The present invention solves the problem of air contamination of injectable low-nitrogen foams by proving alternative syringes which may be easily filled with injectable foam, in a way which avoids the problems described above but which requires little or no intervention by the user to physically remove or purge poor quality foam or air from the syringe. The syringes ensure only consistent and high quality foam is collected for subsequent delivery to the patient. The syringes have typical nozzle, barrel and plunger dimensions, so that they are intuitive for a physician to use and are designed such that they may be filled directly from a source of foam (e.g. by connecting the syringe directly to a pressurised canister device such as those described above) and, after filling, the syringe may be connected directly to a needle, cannula or catheter for administration to a patient.

Accordingly the present invention provides a syringe for dispensing injectable foam comprising:
  a syringe barrel having a nozzle and a bore to receive a syringe plunger;
  a syringe plunger defined by a front end and a rear end connected by a tubular walls and having an internal hollow duct between the front end and the rear end, and through which foam can flow; and
  an injectate chamber formed by insertion of the front end of the plunger into the barrel wherein the injectate chamber comprises a flow disruptor arranged to modify the flow of foam as it enters the injectate chamber.

The flow disruptor typically works by creating a geometric barrier in the flow path of the foam, which forces the foam to flow around the flow disruptor, and thereby reducing velocity of the foam and creating uniform dispersion of the foam into the injectate chamber. Preferably, the flow disruptor is a panel arranged to divert flow of foam radially outwards from the point at which it enters the injectate chamber. The panel is conveniently, but not necessarily planar and in the shape of a disc which ensures uniform dispersion of the foam as it flows around the panel. Preferably the panel is in the form of a baffle, a diffuser, a duck-bill valve or an umbrella valve.

As a result of having a flow disruptor within the injectate chamber, it may be typical that not all of the contents of the injectate chamber will be ejected when the plunger is fully depressed. However, foam sclerotherapy is often conducted under ultrasound guidance, with the physician injecting sclerosing foam until he observes complete filling of the vein/treatment zone with the foam. In this way, the physician often does not need to know the exact volume of foam that has been injected and so, any small dosage discrepancies are thought not to be of significance. In any event, if desired the syringe can be calibrated accordingly to ensure that the administering physician can simply read markings on the barrel wall to determine exactly what volume has been injected.

In general, the syringe has the appearance of a standard syringe with typical syringe dimensions and characteristics e.g. it is typically small dimensions for the injection of small volumes (1 to 20 ml) of foam and which may be easily manipulated by a physician using only one hand. To aid usability the syringe barrel and/or plunger may be fitted with flanges towards their rear to allow for engagement with the physicians fingers and thumb. The syringe nozzle can be concentric or eccentric and can be of a standard type (e.g. Luer connection) to aid connection to needles, cannulas etc. However, as will discussed in more detail below, the syringe plunger and injectate chamber that is formed when the plunger is inserted into the syringe barrel contain structural features that control the way the syringe operates to ensure controlled flow of foam during filling of the syringe, which leads to efficient purging of air which, in turn, provides confidence that as little air as possible is injected into the vein.

The syringe plunger is in the form of a tube with an aperture or opening at each end (the front end or face being defined as the front end because, in use, it is always closer to the syringe nozzle and provides the leading edge during depression of the plunger during injection). A duct lies between the two openings in the plunger through which foam can flow, either to allow the syringe to be filled through the aperture in the rear face of the plunger (by attaching to a source of foam) or to allow waste foam to be collected in the duct, if the syringe is filled through the nozzle. In this regard, the dimensions of the duct can be of any size within the confines of the plunger's tubular but since, during use, the duct will be filled with foam, which will not be expelled from the syringe (or injected into the patient), it is desirable to minimize the total volume of the duct to minimize foam wastage. Typically the duct will be in the form of a narrow tube, which is wide enough to allow connect to a source of foam (e.g. via Luer connection) but, as explained in more detail below, different dimensions and shapes of duct are contemplated with different embodiments of the invention. Although with certain narrow shapes and dimensions of the duct, foam will be retained within the duct without any mechanical closure, in certain embodiments, it is preferred that the duct comprises a one-way valve, which prevents foam from travelling out of the duct and through the aperture in the rear end of the plunger, either during filling of the syringe or during injection of the syringe contents.

The injectate chamber, or dose chamber, of the syringe is formed in the usual way i.e. by insertion of the syringe plunger into the syringe barrel. The syringe is calibrated as is typical for syringes such that the plunger may be withdrawn within the barrel to a point that defines the maximum volume that can be injected to patient/ejected from the syringe nozzle when the plunger is fully depressed. The calibration will take into account any volume occupied by the flow disruptor, as mentioned above.

Typically, the syringe is provided with the plunger partially withdrawn from the barrel to create an injectate chamber of a volume that corresponds to the maximum volume of foam to be injected. In this regard the syringe device can be supplied in a pre-set form depending on the application/volume of foam that is typically injected (for example, 1-2 ml for spider and reticular veins and 5-10 ml for varicose veins). In this "pre-cracked" form, there is very little risk, even with very small syringe volumes, that the plunger may be ejected from the barrel as the syringe is filled with foam from a pressurised source. Syringe filling is accomplished by simply attaching the syringe to a source of foam and filling until the injectate chamber is full (with air being purged and waste removed as discussed below).

The front end of the plunger may have a traditional flat face (i.e. a face which is perpendicular to the plunger walls) but preferably the front face of the plunger has tapered edges which extend radially outwards from the aperture and axially towards the syringe nozzle. In this orientation, the frusto-concial shape around the aperture provides a smooth gradient which aids flow of foam to or from the injectate chamber (depending on how the syringe is filled). Typically this geometry of the front end of the plunger works together with the flow disruptor to control flow or foam but in certain embodiments, it may be the case that the frustoconical shape acts itself like a flow disruptor and no additional structure is needed to ensure smooth flow of foam/filling of the syringe.

As described above, the plunger is structured to allow air to be purged from the syringe as foam travels through the duct. The duct may then be used to trap foam. Preferably, however, the syringe further comprises a vented waste chamber which allows air to pass through but retains foam. The vents may simply be provided in the form of small holes between an inner and outer surface of the waste chamber. If the holes are small enough, they will allow air to pass but the surface tension of to foam will result in the foam being retained within the chamber. Alternatively, the vents may be formed from a hydrophobic material which traps liquid but not gas. Preferably, the vents are in the form of a wettable filter, which allows air to pass through when the filter is dry but when the filter becomes wet due to contact with the foam, the filter is blocked and no material can thereafter pass through. The waste chamber has a volume which corresponds to a volume of foam which may not be of the desired quality for injection. Typically, this equates to less than 5 ml and preferably is in the range of 1-4 ml and more preferably between 1-2 ml. The waste chamber may be transparent so the user can see when foam fills the chamber but conveniently, the waste chamber is made of an opaque material but comprises a transparent window which itself will become opaque when the waste chamber is full of foam.

In one particular embodiment the syringe comprises a waste chamber, which is formed within the internal hollow cavity of the syringe plunger. Preferably, the waste chamber is formed as an area of expanded volume within the duct to allow for a suitable volume of foam to be retained within the waste chamber after the syringe is filled. In this embodiment, the syringe in filled with foam through the syringe nozzle, such that foam travels from a source of foam and into the nozzle. The flow-disruptor is suitably placed to disrupt the flow of foam as it leaves the nozzle and flows into the injectate chamber. Ideally the flow disruptor is in the form of an umbrella valve which has the stem seated within the nozzle and the umbrella valve situated just inside the injectate chamber so that all foam travelling through the nozzle is diverted by the valve. Foam is pushed radially outwards from the valve so that a foam front uniformly travels along the length of the injectate chamber, filling evenly and displacing air as the injectate chamber is filled. Once the injectate chamber is filled, foam will pass through the opening in the front face of the plunger and into the duct within the plunger. In this embodiment, the central volume of the duct is expanded to accommodate a larger volume of foam (e.g. 1-2 ml). Because the waste chamber is vented to air, any air which is displaced by the foam will be vented and the waste chamber completely filled with foam. The waste chamber also comprises a window so that the user can see when the waste chamber is full. At this point the source of foam may be stopped and/or removed. However, even is the source of foam is not stopped immediately, the waste chamber may overflow into the remaining volume of the duct (towards the rear end of the plunger) until it comes into contact with a one way valve, which prevents foam from escaping the syringe. As soon as the waste chamber is observed to be filled, the source of foam may be removed and the syringe contents injected.

In another particular embodiment, the waste chamber has the same features as described above (vents, window etc) but is provided externally to the syringe but detachably connected to the syringe through the nozzle. In this embodiment, the syringe is filled with foam through the rear end of the plunger to displace air through the waste chamber, and fill the injectate chamber after the waste chamber has been filled with foam. The aperture in the rear end of the syringe plunger is of a dimension that enables direct attachment to a source of foam such as the valve stem of a pressurised canister or via suitable tubing to a source of foam. As foam enters through the rear face of the plunger, it passes through a one-way valve and fills the duct in the plunger. As foam continues to travel from the duct and into the injectate chamber, it comes into contact with the flow disruptor where the flow is modified to ensure uniform filling of the injectate chamber. In this embodiment, the flow disruptor is attached to the opening in the front face of the plunger so that all of the foam is forced through it. The disruptor may be in the form of a baffle plate, a duck-bill valve or an umbrella valve. Preferably, the disruptor is an umbrella valve of suitable dimensions to be inserted into the opening in the front face of the plunger to ensure all foam travels through the valve. The front face of the plunger is conveniently formed with edges which are taped radially outwards from the opening, to further support flow of foam from the disruptor and into the injectate chamber in a uniform fashion. Foam then fills the injectate chamber. As the chamber is being filled, a foam front (or foam plug) is formed which is sufficiently coherent to displace any air from the flow path: air is displaced from the injectate chamber as it fills and through the nozzle and into the waste chamber where it is vented. Foam flow is then continued until the waste chamber is full—observed by a transparent window in the waste chamber being filled with foam. At this point, the flow of foam may be stopped and removed from the syringe. The waste chamber may then simply be removed from the syringe nozzle and discarded and the syringe contents injected.

In this embodiment, it is preferred that the external waste chamber contains two chambers connected by an opening such that in use, the first chamber fills with foam and then enters the second chamber. Typically in this format the second chamber is vented, although either or both may be vented. The relative dimensions and shapes of each chamber may be modified to control the total volume of foam it can contain. For example, in most applications, the volume of poor quality foam that should be retained within waste is in the order of 1-2 ml. Larger outer volume waste chambers can be convenient for handling purposes (ease of attachment and detachment) but the inner volume need only be large enough to contain the necessary volume of poor quality foam. In this way wastage of good quality foam is minimised.

Waste chambers as described above form a second aspect of the present invention.

In a third aspect the present invention provides a kit for dispensing medical grade injectable foam comprising a syringe as described above together with a source of foam. Preferably, the source of foam is a pressurised canister containing liquid sclerosing agent and gas under pressure. The syringe is designed to be connected (for example by Luer attachment) directly the canister when it may be filled by actuating the canister valve. Typically this is done by pressing down on the syringe flanges when it is attached to the canister to depress the valve and start the flow of foam.

In another aspect, the invention provides a method of dispensing foam comprising: connecting the syringe to a source of foam, dispensing a continuous flow of foam into the syringe from the source whereby the flow of foam displaces air through the waste chamber, fills or substantially fills the waste chamber with foam and fills the injectate chamber after the waste chamber has been filled.

The invention will now be described by way of example with reference to the following figures.

Figure 1:
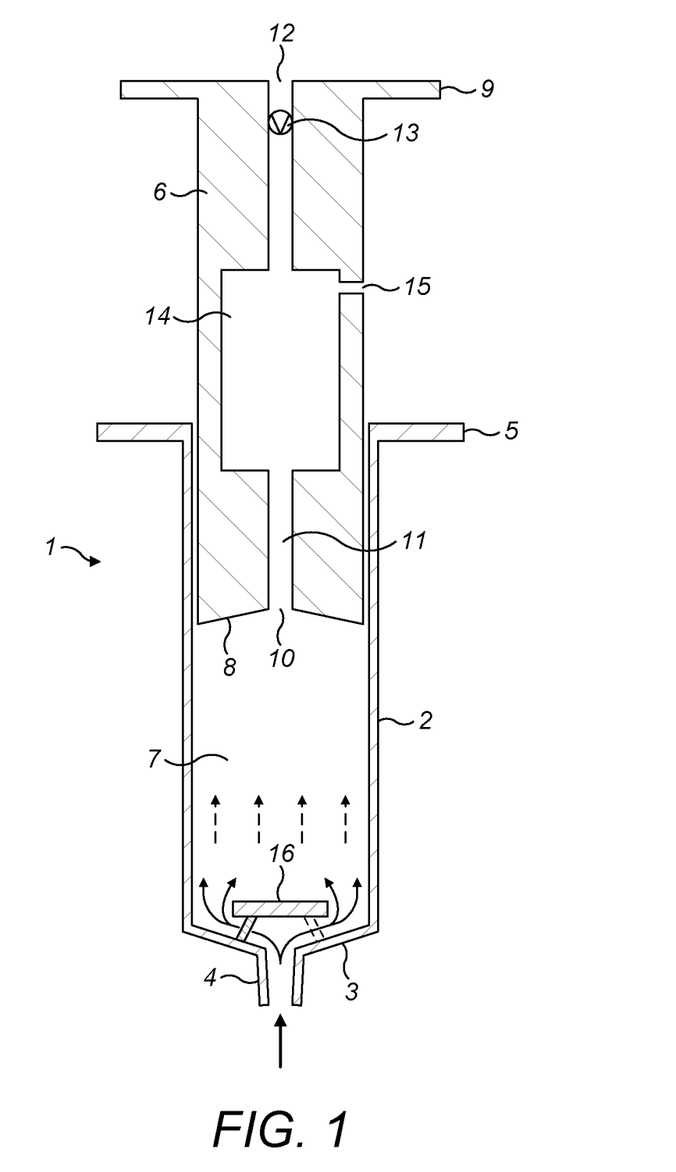
FIG. 1 shows a schematic cross sectional view of an embodiment of the invention in which the vented waste chamber is internal to the syringe plunger

Referring to FIG. 1, the syringe [1] comprises a barrel [2] of conventional cylindrical shape with a front end wall [3] in which is located a conventional Luer nozzle [4] and an opening in the rear. Flanges [5] are located around the rear end opening to provide finger grips as is conventional. The bore extending from the rear end opening in the plunger accommodates a tubular plunger [6] which forms a seal when inserted into the barrel and creates an injectate chamber [7] which corresponds to the dose volume of the syringe. In this embodiment the syringe is provided in the shown "pre-cracked" position i.e. with the plunger withdrawn to predefined position which corresponds to the maximum volume that can be ejected from the syringe.

A flow disruptor [16] in the form of a baffle plate is located adjacent the nozzle [4] and attached by a number of legs or stems [17] to the front face [3] of the syringe barrel. The baffle plate is formed as a planar disc of suitable plastics or metallic material. Although not shown in FIG. 1, the baffle plate may be substituted with a duck-bill or umbrella valve which can be housed directly on the inside of the nozzle [4]. This may be advantageous in reducing manufacturing complexity as such valves can be designed to be snap fitted into the nozzle.

The plunger [6] is of tubular design and formed of a plastic moulding having a front end [8] and a rear end which contains flanges [9] to provide finger grips. The front end of the plunger has towards its centre an aperture [10]. The aperture [10] creates an opening to a duct [11] which extends between the aperture [10] in the front end of the plunger and another aperture in the rear end of the plunger [12]. The duct is of suitable cross sectional diameter to allow foam to flow through it as the syringe is filled. Housed within the duct, towards the rear end of the plunger, is a valve [13], typically duck-bill or umbrella valve which prevents foam from escaping the rear end of the plunger. Alternatively the valve [13] may take the form of a wettable filter which allows air to pass but becomes closed as the filter is wetted after contact with foam.

The central portion of the duct [11] is of expanded cross sectional diameter to create an internal waste chamber [14], which is, optionally, vented either through one or more side vents [15].

In use, the syringe is connected to a source of foam (not shown) which is typically a pressurised canister of the type described in WO 00/72821 and WO 02/41872. The syringe may be connected directly through the nozzle or by inserting the nozzle into a tube which conveys foam from a source. Foam flows into the syringe as depicted by the arrows in FIG. 1 i.e. foam enters the syringe nozzle [4] and its flow path is immediately diverted by the baffle [16] as it leaves the nozzle and enters the injectate chamber [7]. The baffle directs the foam towards the tubular side walls of the syringe, such that, initially, the injectate chamber fills more rapidly around the outside of the chamber. Very quickly, however, the flow of foam moves around the upper surface of the baffle and the net effect is that a uniform foam front (depicted by dotted arrows) is created which is observed in the form of an even "pillar" of foam rising up through the injectate chamber. The foam front acts like a piston which pushes air out of the injectate chamber and through the duct and waste chamber where it is vented through the vent [15] (N.B. the vent may take any pathway between the waste chamber and the external wall of the plunger for example, through the rear end).

When the injectate chamber is full of foam (and air has been expelled), foam continues to travel through the aperture in the front face of the plunger [10] and into the duct [11] and onwards into the waste chamber [14]. The flow pattern at this stage is less controlled but flow is continued until the waste chamber is full. This can be judged by simply allowing foam flow to continue for a few seconds after the injectate chamber is observed as full but more conveniently the plunger and hence the waste chamber is formed of a transparent material so that it is clear when the chamber is full. Alternatively, the plunger is formed of an opaque plastics materials, the waste chamber may contain a small transparent window, which will be rendered opaque as the window is covered with foam. The window arrangement is not shown in FIG. 1 but it will be understood that arrangements such as those shown in FIGS. 2 and 3 can be easily adapted for use in the syringe of FIG. 1 by creating a window in the opaque plunger which is near the rear end of the waste chamber.

When the waste chamber is observed as full, the source of foam may be stopped and/or removed. Excess foam (greater than the volume of the waste chamber) fills the upper part of the duct but is prevented from escaping the rear of the syringe by valve [13]. With the source of foam removed, the syringe is ready for use in the conventional way i.e. a needle or cannula is attached to the nozzle and the plunger [6] is depressed to expel the contents of the injectate chamber [7] through the nozzle and into the patient. The syringe is calibrated such that the plunger need only be depressed to administer a desired volume (e.g. 1 ml). The remaining volume may then be used for a subsequent injection or may be discarded. If or when the plunger is fully depressed in the barrel, it will be apparent that not all of the foam will be expelled from the chamber as the front face of the plunger [8] meets the baffle [16].

The relative shapes and dimensions of the front face of the plunger and the baffle are illustrative only in FIG. 1 and other shapes are contemplated within the scope of the invention to minimize the volume of foam that is retained within the syringe. For example, the front face [8] is shown as extending radially outwards (frustoconical) as this improves foam flow from the injectate chamber into the duct (and waste chamber) but equally the face can be flat and planar such that it contacts the upper face of the baffle [16] when the plunger is fully depressed. It will be understood that, whatever the relative shapes of the flow disruptor and plunger face and the corresponding volume of foam that is retained within the injectate chamber, the syringe may be calibrated as is conventional in the art to ensure that the actual volume injected from the syringe is known.

When the plunger is fully depressed in the barrel, there will also be foam retained within the waste chamber [14] and the duct [11]. The relative dimensions of the duct (and the surface tension of the foam) are such the foam will be retained in the duct and chamber during injection.

When foam administration is complete, the syringe may be disposed of in accordance with routine clinical procedures.

Figure 2:
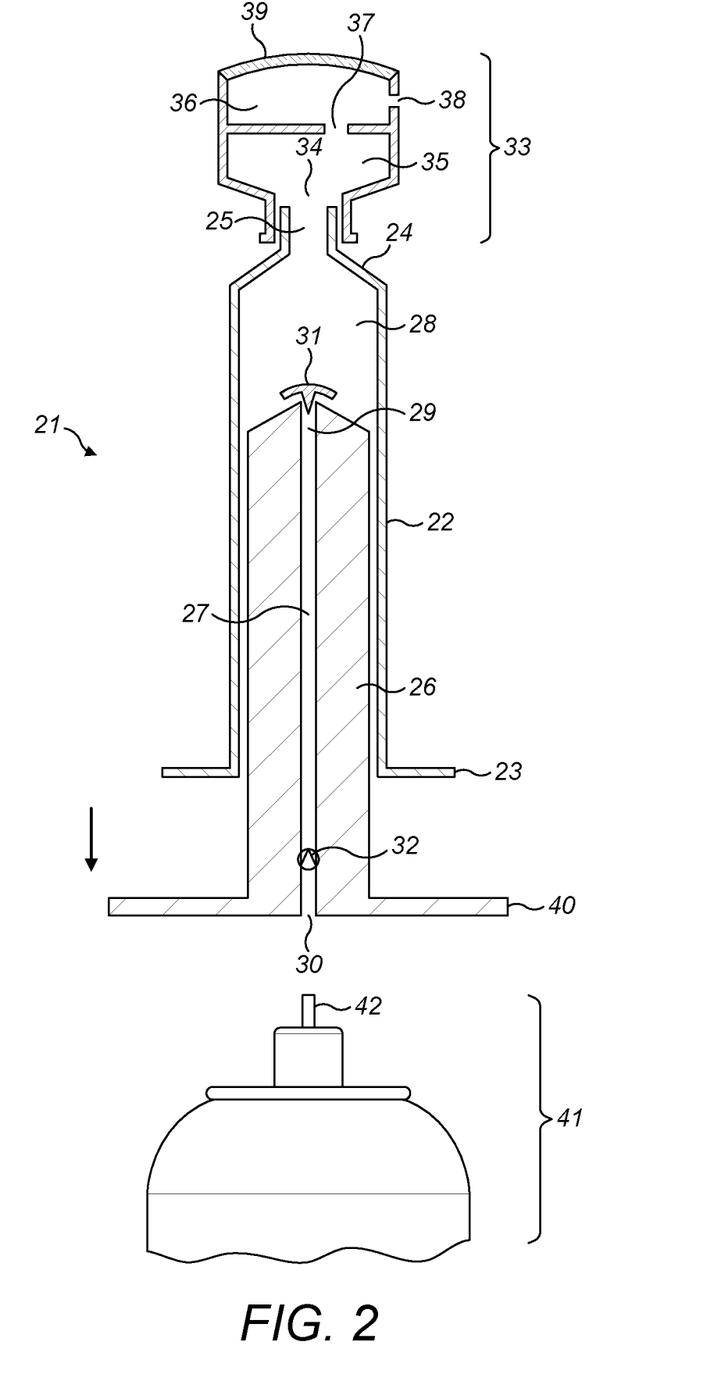
FIG. 2 shows a schematic cross sectional view of another embodiment of the invention which comprises an external waste chamber which is detachably connected to the syringe nozzle

FIG. 2 shows an embodiment of the invention in a "rear-fill" format. The syringe [21] comprises a barrel [22] with rear end flange [23], a front face [24] and conventional nozzle [25] which are all similar to the corresponding parts in FIG. 1.

In this embodiment, the syringe plunger [26] is formed of a tubular plastics material and forms a seal when inserted into the barrel in the conventional way. Typically, although not necessary, the syringe is provided in a "pre-cracked" form such that an injectate chamber [28] is created of a defined volume, which typically corresponds to the maximum volume of foam to be administered in a single injection. Similar to embodiment shown in FIG. 1, the plunger has a duct [27] which runs through the length of the plunger, between an opening [29] in the front face of the plunger and an opening [30] at the rear. The opening [29] in the front face of the plunger has, inserted into it, a flow disruptor in the form of an umbrella valve [31], which directs flow of foam radially outwards from the opening as foam passes through it. Situated close or adjacent the opening [30] in the rear of the plunger is an optional one-way valve [32] which is arrange to permit flow of foam through the duct from rear to front but prevents back-flow of foam during filling and subsequent administration.

Connected to the syringe nozzle, by conventional means such as a Luer lock, is an external waste chamber [33]. The waste chamber [33] comprises an opening which is configured to provide a seal when connected to the nozzle and is detachable. The waste chamber is formed of a suitable plastic moulding and has an inner volume which corresponds to the maximum volume of waste foam that can be accommodated, typically between 1 and 5 ml. The inner volume is divided into two chambers, a lower chamber [35] and an upper chamber [36] which are in fluid communication with each other through an opening [37]. The waste chamber further comprises one or more vents [38] to enable venting/purging of air from the system. The vent is shown positioned in a side wall but may be positioned anywhere within the chamber. The two chamber arrangement is not essential and a single chamber waste chamber may be sufficient, similar to the dimensions shown in FIG. 1. However, the two chamber arrange depicted in FIG. 2 is advantageous because it assists with pressure equalization when the syringe is filled from a pressurised source of foam and slows down the filling of the waste chamber. Since the source is provided from a source which is under pressure, if pressure is not allowed to equalize, foam may spurt from the syringe nozzle when the waste chamber is removed. The upper wall of the waste chamber [39] is formed of a transparent material so as to provide a window such that the user can readily determine when the waste chamber is full. Alternative arrangements or positions of the window are, of course, possible, for example a portion of the side walls of the chamber can be made transparent or the entire chamber can be formed from a transparent material.

The syringe is designed to be filled from the rear i.e. through the opening [30] in the rear of the plunger. The plunger has extended (length) flanges [40] at its rear end to facilitate handling during connection of the syringe to a source of foam, here shown as a pressurised canister device [41] of the type described in WO 00/72821. The dimensions of the opening [30] are selected to enable a female/male connection to the valve stem [42] on the pressurised canister [41].

In use, the syringe [21], with waste chamber [33] connected to the nozzle [25], is connected to the valve stem [42] on the pressurised canister [41]. The syringe and valve stem are pressed down by pushing on the extended flanges [40] to actuate the valve and start the flow of foam. Foam flows into the syringe, through the duct [27] until it reaches the umbrella valve [31], where it is forced radially outwards to ensure even filling of the injectate chamber (flow is controlled and air is purged in the same way as described for the embodiment in FIG. 1).

When the injectate chamber is filled, foam flows out through the syringe nozzle [25] and starts to fill the waste chamber. When the transparent window [39] is obscured by being covered by foam, the user may release the valve [42] by removing the pressure applied to the extended flanges [40].

Once the syringe is filled, the syringe may be removed from the canister [41], the waste chamber [33] removed and discarded and the syringe and its contents are ready for administration to a patient. If desired an additional valve (not shown) may be inserted into the opening [34] of the waste chamber to ensure that no waste foam leaks from the waste chamber after it has been disconnected from the syringe.

FIG. 3 shows an alternative arrangement of the example described above (FIG. 2). FIG. 3a shows a rear-fill syringe [301] comprising a conventional, calibrated barrel [302] with a Luer lock nozzle [303] and rear flanges [304]. A rear-fill plunger [305] is partially inserted into the barrel [302] to define an injectate chamber [307] and has at its rear end, expanded flanges [306] to assist in connecting the rear end of the syringe to a source of foam (not shown).

Figure 3A:
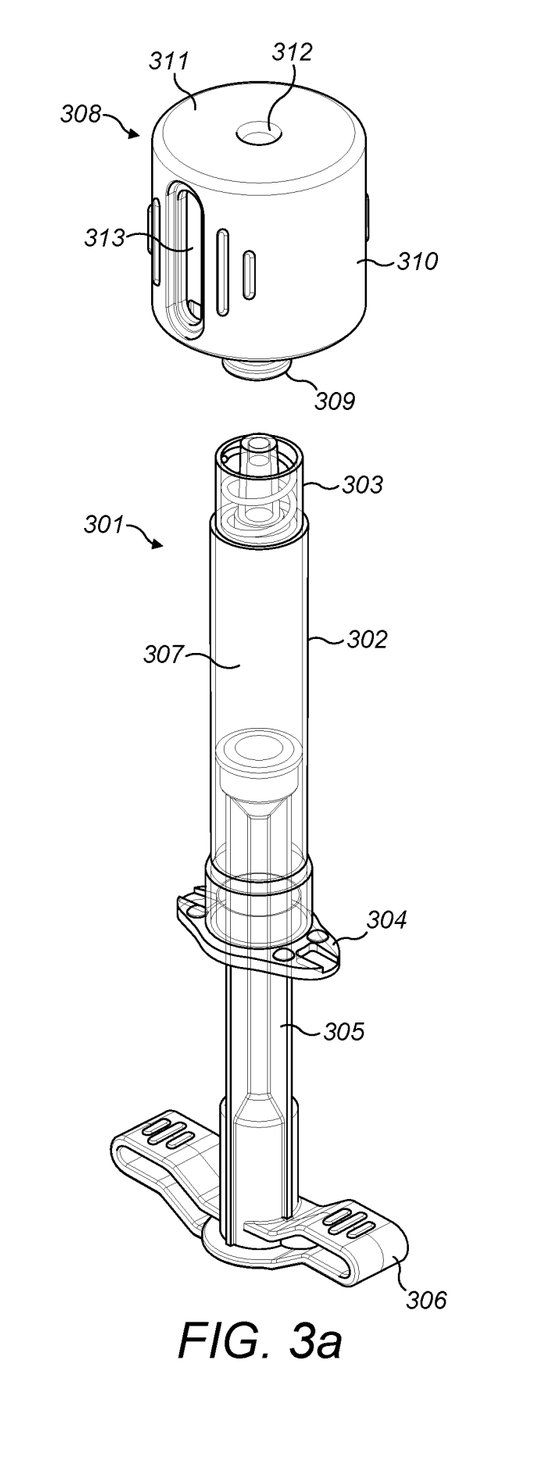
FIG. 3 shows a schematic cross sectional view of an alternative arrangements of the embodiment shown in FIG. 2

An external waste chamber [308] is configured with a Luer connection [309] to ensure a detachable sealed connection with the syringe nozzle [303]. The waste chamber has a tubular wall [310] and an upper wall [311] which house a two-chamber waste volume (shown in more detail in FIG. 3b). The upper wall [311] comprises a vent-hole [312] to allow air to escape when in use. The waste chamber has a transparent window [313] situated in the side wall [310] which, as is explained in more detail below, is arranged to provide an visual indicator when the waste chamber is full of foam.

Figure 3B:
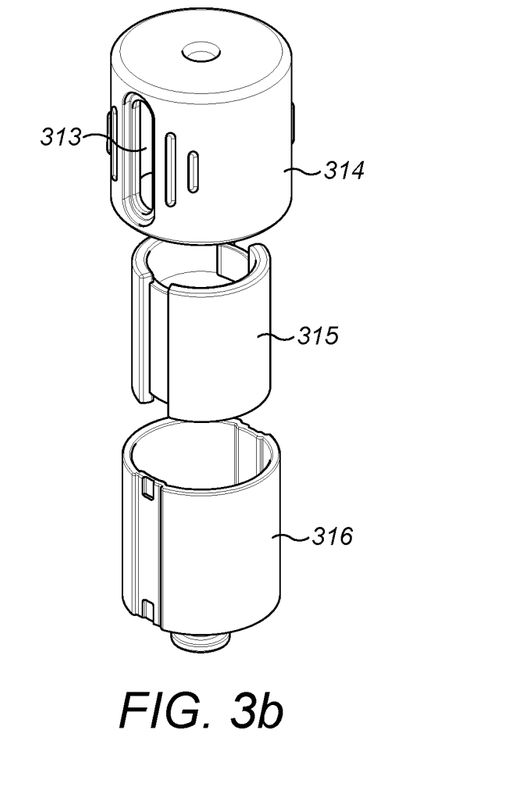

FIG. 3b shows an expanded view of the waste chamber [308]. The waste chamber is made of three parts which are snap-fitted together: an outer housing [314] comprising a window [313], a divider component [315] which divides the inside of the waste chamber into two distinct but connected chambers and a third inner component which provides a pathway for foam to pass and fill the space immediately behind the window [313]. The process by which the waste chamber is filled is the same as that described for FIG. 2 but the flow path is different, as discussed in more detail below.

Figure 3C:
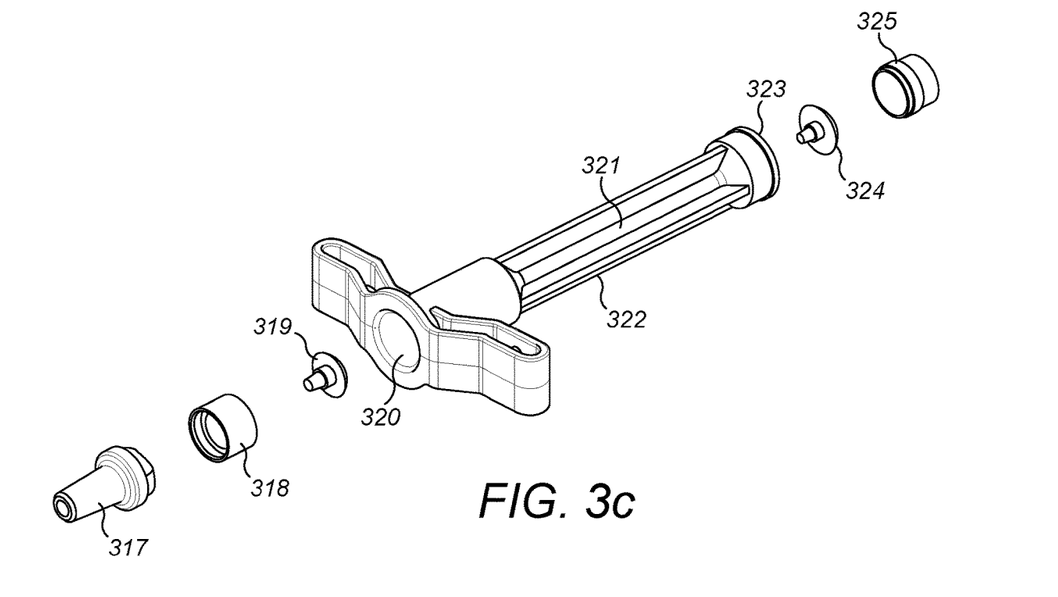

FIG. 3c shows an expanded view of the plunger [305] which comprises a connector [317] to enable connection to a source of foam (typically a pressurised canister), a valve housing [318] which houses an umbrella valve [319] which is arranged to allow flow of foam from the rear of the plunger as described for FIG. 2. The connector [317], valve housing [318] and the valve [319] all inserted into the rear of the plunger [320] to create a foam path which extended through a narrow duct [321] housed within the main body of the plunger [322]. There is an expanded volume opening at the front face of the plunger into which is inserted a second umbrella valve [324] with associated housing [325].

Figure 3D:
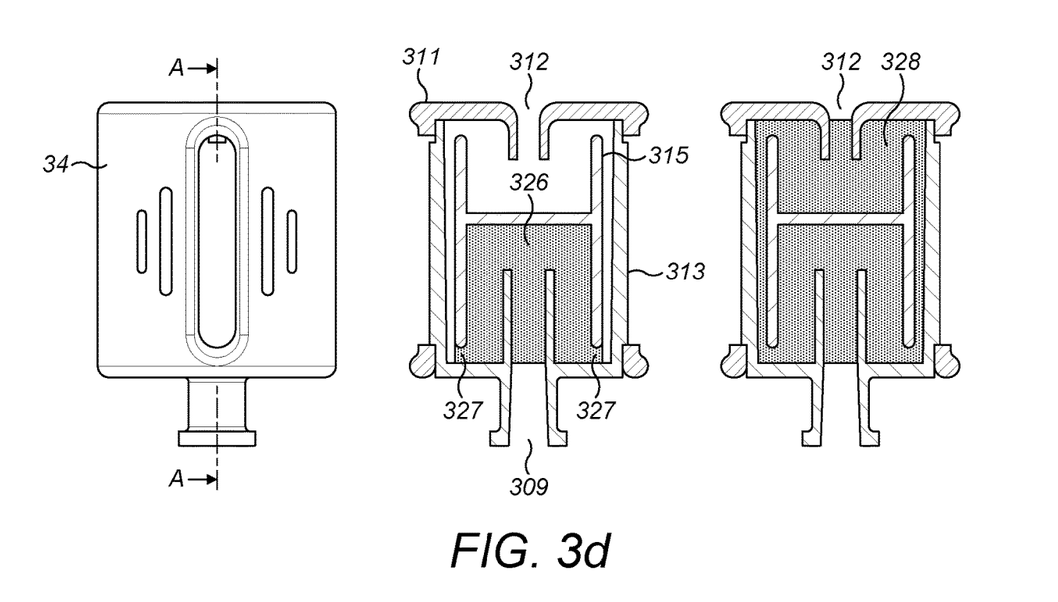

FIG. 3d shows the waste chamber of FIG. 3b in cross section along the line A-A. In use, foam enters the waste chamber via the opening [309] where it fills the lower chamber [326] created by the divider insert [315] and passes through aperture [327] and travels up through the gap between the divider [315] and the window [313]. When the gap is filled, the window is obscured by foam, indicating to the uses that sufficient foam has been collected in the waste chamber. Any additional foam then flows into the upper chamber [328] which is vented through hole [312] to enable air to escape. The upper chamber allows for the collection of additional foam that results from the natural lag time between observing the window full of foam and actually removing or stopping the flow of foam from the source.

Figure 4:
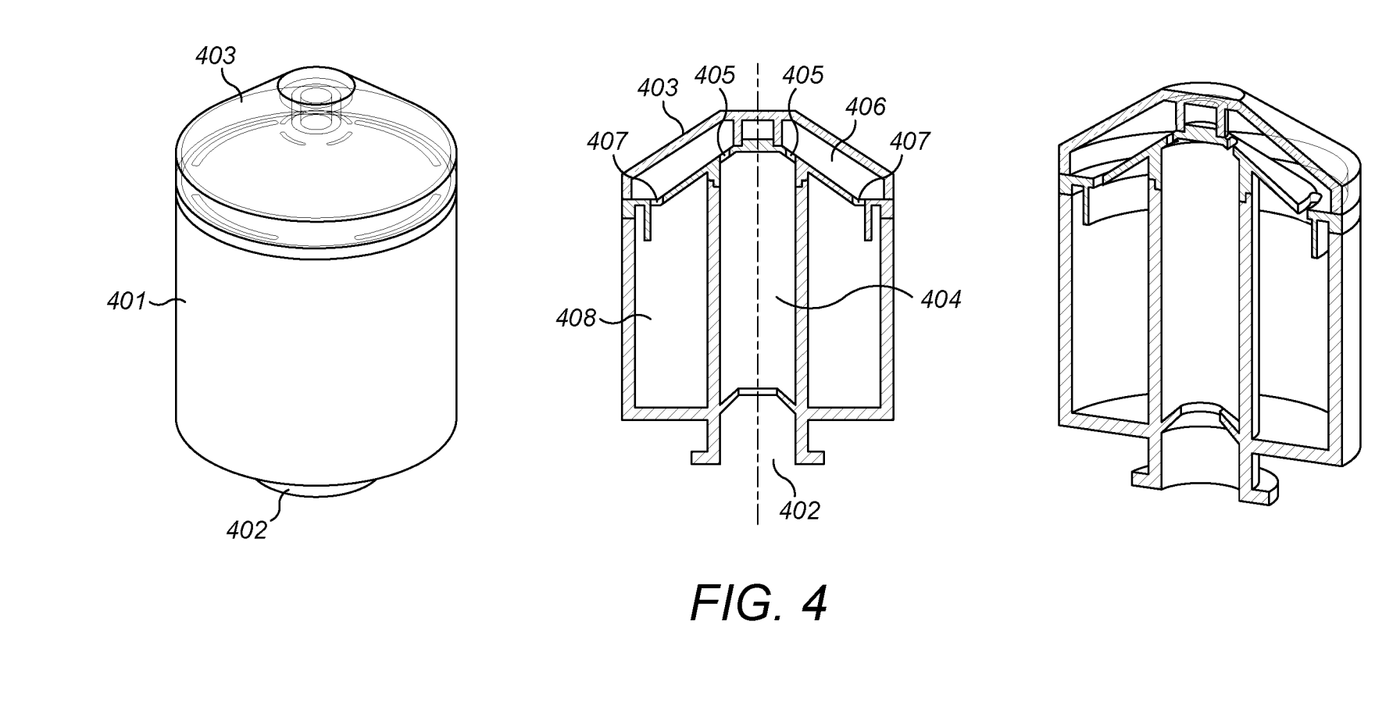
FIG. 4 shows alternative configurations of external waste chambers in cross section.

FIG. 4 shows an alternative configuration of an external waste chamber of the invention which operates on a similar principle to that of FIG. 3d but which is configured to reduce the total fillable volume of the waste chamber. It is important, particularly for small volume applications (e.g. the treatment of spider and reticular veins) that no more foam than is necessary is wasted. This embodiment has the advantage of having a sufficiently large outside volume to enable ease of attachment and detachment but a small internal volume to reduce foam wastage. FIG. 4 shows an external waste chamber [401] with generally cylindrical outer walls, a lower wall with fluid connector [402] for sealable attachment to a source of foam and an upper wall [403] which is transparent to provide a visual indication that the waste chamber is full of foam. Foam enters the waste chamber through opening [402] and travels through inner pathway [404]. Apertures [405] at the upper end of the pathway allow foam to travel from the inner pathway into an upper chamber [406]. The upper chamber [406] comprises the upper transparent wall [403] which is obscured as the upper chamber is filled with foam. With this visual indicator, the user can stop the flow of foam. The upper chamber also comprises apertures [407] through which excess foam can flow into a waste reservoir [408] to allow for additional foam flow in the lag time between the upper chamber being filled and the user stopping or disconnecting the flow of foam from the source.

The invention claimed is:

1. A syringe for dispensing injectable foam comprising:
   a syringe barrel having a nozzle and a bore to receive a syringe plunger;
   a syringe plunger defined by a front end and a rear end connected by tubular walls and having an internal hollow duct between the front end and the rear end, and through which foam can flow, the internal hollow duct including a one-way valve which prevents foam from travelling out of an aperture in the rear end of the plunger; and
   an injectate chamber formed by insertion of the front end of the plunger into the barrel, and which comprises a flow-disruptor attached to the barrel and arranged to modify the flow of foam as it enters the injectate chamber.

2. The syringe according to claim 1 wherein the flow disruptor is a panel arranged to divert flow of foam radially outwards from the point at which it enters the injectate chamber.

3. The syringe according to claim 2 wherein the panel is disc shaped and is a baffle, a diffuser, a duck-bill valve or an umbrella valve.

4. The syringe according to claim 3 wherein the syringe is provided with the plunger partially withdrawn from the barrel to create the injectate chamber with a volume that corresponds to the maximum volume of foam to be injected.

5. The syringe according to claim 2 wherein the syringe is provided with the plunger partially withdrawn from the barrel to create the injectate chamber with a volume that corresponds to the maximum volume of foam to be injected.

6. The syringe according to claim 1 wherein the syringe is provided with the plunger partially withdrawn from the barrel to create the injectate chamber with a volume that corresponds to the maximum volume of foam to be injected.

7. The syringe according to claim 1 wherein the front end of the plunger has tapered edges which extend radially outwards from an aperture and axially towards the syringe nozzle.

8. The syringe according to claim 1, further comprising a vented waste chamber which allows air to pass through but retains foam.

9. The syringe according to claim 8 wherein the waste chamber comprises a transparent window which becomes opaque when the waste chamber is full of foam.

10. The syringe according to claim 9 wherein the waste chamber is disposed within the plunger such that the syringe is filled with foam through the nozzle to displace air through the waste chamber and when the injectate chamber is filled, foam flows through the internal hollow duct into the waste chamber.

11. The syringe according to claim 8 wherein the waste chamber is disposed within the plunger such that the syringe is filled with foam through the nozzle to displace air through the waste chamber and when the injectate chamber is filled, foam flows through the internal hollow duct into the waste chamber.

12. The syringe according to claim 1, further comprising a vented waste chamber connected to the internal hollow duct and which allows air to pass through but retains foam.

13. A kit for dispensing medical grade injectable foam comprising a syringe according to claim 1 and a source of foam.

14. The kit according to claim 13 wherein the source of foam is a pressurized canister containing liquid sclerosing agent and gas under pressure.

15. A method of dispensing foam comprising:
    connecting the syringe according to claim 7 to a source of foam; and
    dispensing a continuous flow of foam into the syringe from the source, whereby the flow of foam displaces air through the waste chamber, fills or substantially fills the waste chamber with foam and fills the injectate chamber after the waste chamber has been filled.

16. A syringe for dispensing injectable foam comprising:
    a syringe barrel having a nozzle and a bore to receive a syringe plunger;
    a syringe plunger defined by a front end and a rear end connected by tubular walls and having an internal hollow duct between the front end and the rear end, and through which foam can flow, the internal hollow duct including a one-way valve which prevents foam from travelling out of an aperture in the rear end of the plunger;
    an injectate chamber formed by insertion of the front end of the plunger into the barrel, and which comprises a flow-disruptor arranged to modify the flow of foam as it enters the injectate chamber; and
    a vented waste chamber which allows air to pass through but retains foam;
    wherein the waste chamber is present within the internal hollow duct of the syringe plunger such that the syringe is filled with foam through the syringe nozzle.

* * * * *